(12) United States Patent
Buhren et al.

(10) Patent No.: US 8,142,485 B2
(45) Date of Patent: Mar. 27, 2012

(54) BONE CONNECTION DEVICE

(75) Inventors: Volker Buhren, Murnau (DE);
Christian Lutz, Mönckeberg (DE)

(73) Assignee: Stryker Trauma SA (CH)

( * ) Notice: Subject to any disclaimer, the term of this patent is extended or adjusted under 35 U.S.C. 154(b) by 960 days.

(21) Appl. No.: 12/157,391

(22) Filed: Jun. 10, 2008

(65) Prior Publication Data
US 2008/0249573 A1    Oct. 9, 2008

Related U.S. Application Data

(63) Continuation of application No. 10/803,638, filed on Mar. 18, 2004, now abandoned.

(30) Foreign Application Priority Data

Mar. 20, 2003  (CH) .................................. 481/03

(51) Int. Cl.
*A61B 17/80* (2006.01)
(52) U.S. Cl. ....................................................... 606/289
(58) Field of Classification Search ............... 606/61, 606/69–73
See application file for complete search history.

(56) References Cited

U.S. PATENT DOCUMENTS

| | | |
|---|---|---|
| 1,025,008 A | 4/1912 | Miner |
| 1,150,114 A | 8/1915 | Hays |
| 2,301,244 A | 11/1942 | Bishop |
| 2,301,590 A | 11/1942 | Signorelli |
| 2,612,073 A | 9/1952 | Taylor |
| 2,836,214 A | 5/1958 | Rapata |
| 3,534,731 A | 10/1970 | Muller |
| 3,547,114 A | 12/1970 | Haboush |
| 3,566,947 A | 3/1971 | Jukes |
| 3,596,656 A | 8/1971 | Kaute |
| 3,825,048 A | 7/1974 | Triska |
| 4,240,323 A | 12/1980 | Kojima |
| 4,276,806 A | 7/1981 | Morel |
| 4,325,665 A | 4/1982 | Jukes |
| 4,352,589 A | 10/1982 | Allison et al. |
| 4,388,921 A | 6/1983 | Sutter et al. |
| 4,405,272 A | 9/1983 | Wollar |
| 4,484,570 A | 11/1984 | Sutter et al. |
| 4,493,317 A | 1/1985 | Klaue |
| 4,657,458 A | 4/1987 | Wollar et al. |
| 4,692,290 A | 9/1987 | Steele et al. |
| 4,729,704 A | 3/1988 | Yokoyama |
| 4,794,918 A | 1/1989 | Wolter et al. |
| 4,828,441 A | 5/1989 | Frasca |
| 4,867,144 A | 9/1989 | Karas et al. |
| 4,905,680 A | 3/1990 | Tunc |
| 4,952,107 A | 8/1990 | Dupree |
| 4,964,403 A | 10/1990 | Karas et al. |
| 5,002,544 A | 3/1991 | Klaue et al. |
| 5,013,313 A | 5/1991 | Surer |
| 5,041,113 A | 8/1991 | Biedermann et al. |
| 5,053,036 A | 10/1991 | Perren et al. |
| 5,057,111 A | 10/1991 | Park |

(Continued)

*Primary Examiner* — William H. Matthews
(74) *Attorney, Agent, or Firm* — Lerner, David, Littenberg, Krumholz & Mentlik, LLP

(57) ABSTRACT

An implantable orthopedic device having a load-bearing element, such as a bone plate, with at least one opening for a fixation element and one insert which can be inserted in an inclined opening in a receptacle in the bore. This insert has an external form that is at least partially complementary to the internal form of the receptacle and a central through-bore for receiving the body of the fixation element such as a bone screw. The insert also provides a locking system for holding the insert in the receptacle, in which the insert exhibits at least one locking mechanism with which conformal locking with the load-bearing element may be achieved.

19 Claims, 3 Drawing Sheets

U.S. PATENT DOCUMENTS

| | | |
|---|---|---|
| 5,065,490 A | 11/1991 | Wivagg et al. |
| 5,090,854 A | 2/1992 | Hafeli et al. |
| 5,108,399 A | 4/1992 | Eitenmuller et al. |
| 5,127,914 A | 7/1992 | Calderale et al. |
| 5,129,899 A | 7/1992 | Small et al. |
| 5,147,363 A | 9/1992 | Harle |
| 5,151,103 A | 9/1992 | Tepic et al. |
| 5,209,751 A | 5/1993 | Farris et al. |

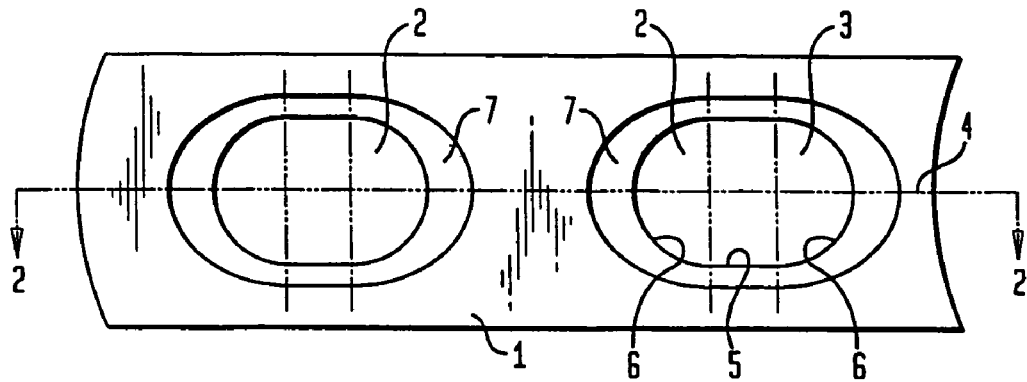
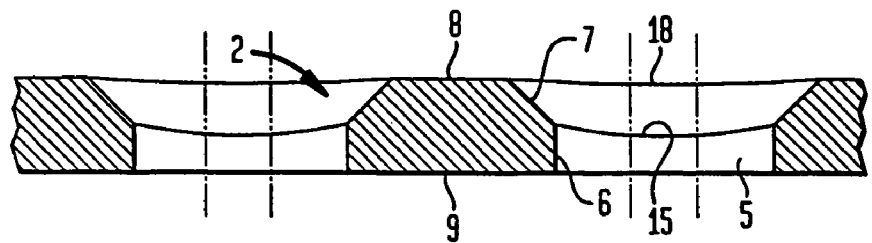
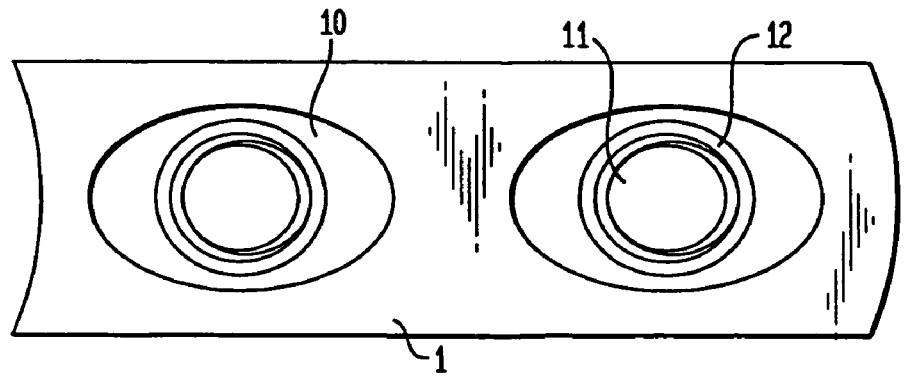
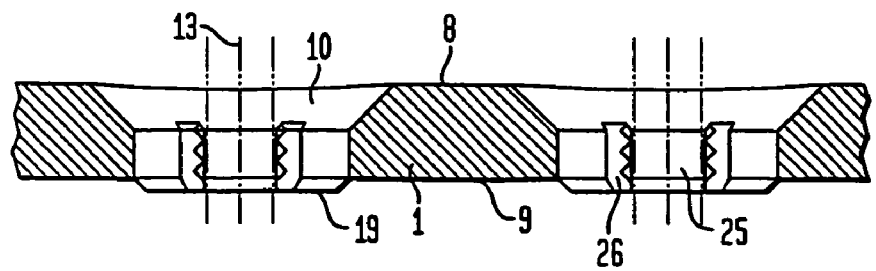

BONE CONNECTION DEVICE

CROSS-REFERENCE TO RELATED APPLICATION

This application is a continuation of U.S. application Ser. No. 10/803,638, filed on Mar. 18, 2004, now abandoned and the disclosure of which is incorporated herein by reference.

BACKGROUND OF THE INVENTION

The invention concerns an implantable orthopedic device with a load-bearing element such as a bone plate, with at least one opening for a fixation element such as a bone screw. An insert is provided that can be inserted into the opening in a receptacle in which the external shape of the insert is at least partially complementary to the internal shape of the receptacle. The insert has a central through-bore for mounting a body of the fixation element. The implantable orthopedic device has a structure for holding the insert in the receptacle.

A series of implantable orthopedic devices with load-bearing elements, such as bone plates, with openings for the insertion of fixation elements in such load-bearers are known from the prior art. Among them are proposals for the mono-axial as well as poly-axial attachment of fixation elements, particularly screws.

As an example for a device of this type having poly-axial attachment of screws in load-bearing elements is shown in U.S. Pat. No. 5,954,722. Other bone plates with inserts are shown in U.S. Pat. Nos. 5,976,141 and 5,607,428.

Among the proposals in the prior art is WO 00/53110 (U.S. Patent Publication No. 2002/0045901) which publication relates to an elongated bore in a load-bearing element, which is, on one end, semicircular with rounded-off edges, and which exhibits on the opposing end what essentially is a half thread. The threaded end extends at an angle of more than 180 degrees. With this, it is possible to screw a screw into the threaded side at right angles to the load-bearing element, so that the screw is also firmly connected to the load-bearing element. On the opposite side of the bore, it is possible to screw in a screw at a desired angle perpendicular to the load-bearing element, particularly poly-axially. These screws are, however, not stably locked in the axial direction.

The prior art exhibits the disadvantage that the screws are intended exclusively for insertion with specifically designed load-bearing elements, and thus only a specific type of insertion, such as, for example, poly-axial attachment or mono-axial attachment, is possible. Inserts for bone plates are known from U.S. Pat. No. 5,190,545.

SUMMARY OF THE INVENTION

It is an object of the invention to improve the prior art devices in such a way that a true variety of screws or other means of attachment for various types of attachment can be inserted.

This object is achieved by an insert which can be engaged with the load-bearing element in a manner which results in the insert being firmly fixed. With a suitable insert, an angled position and specifically any desired defined angular position can be obtained. Of particular advantage is that the secure fixing of the insert can be assured directly and automatically with the insertion of the fixation element.

These and other objects of the invention are achieved by an implantable orthopedic device or bone stabilization device comprising an elongated bone plate having a plurality of apertures extending through the bone plate. At least one insert is provided having a body with a threaded bore and outer surface for engaging an inner surface of the aperture. At least part of the aperture is surrounded by a locking surface and the insert outer surface has a resilient extension for engaging the locking surface. Thus, the insert may be inserted into the aperture from a top surface of the plate with a resilient extension engaging the locking surface in the aperture thereby resiliently coupling the plate in the insert. The threaded bore of the insert could be angled with respect to the top surface of the plate or could be perpendicular thereto. Preferably, the axis of the aperture extending from a top plate surface to a bottom plate surface is perpendicular to the plate top and bottom surfaces. The locking surface could be a ledge or a ridge extending at least partially around the inner surface of the aperture or one could utilize the bottom plate surface as a ridge for engaging the resilient extensions of the insert. The extension on the insert may have an outwardly extending lip which engages under the ledge or plate bottom surface to prevent the insert from being removed from the aperture.

Through the provision of a kit with various inserts with inclined axes, and inner bores on which the screws can be mounted, the surgeon can be provided with a bone plate able to orient bone screws at a number of defined angles in a simple manner. For this reason, the insert is provided with an oval configuration.

BRIEF DESCRIPTION OF THE DRAWINGS

The present invention will be better understood on reading the following detailed description of non-limiting embodiments thereof, and on examining the accompanying drawings, in which:

FIG. 1 is a top view of a load-bearing element in the form of a bone plate with a row of attachment bores according to a first embodiment of the invention;

FIG. 2 is a sectional side view of the load-bearing element according to FIG. 1 along lines 2-2;

FIG. 3 is a top view of the load-bearing element according to FIG. 1 with the insert of the present invention inserted therein;

FIG. 4 is a sectional side view of the load-bearing element with insert inserted according to FIG. 3;

DETAILED DESCRIPTION

Figure 5:
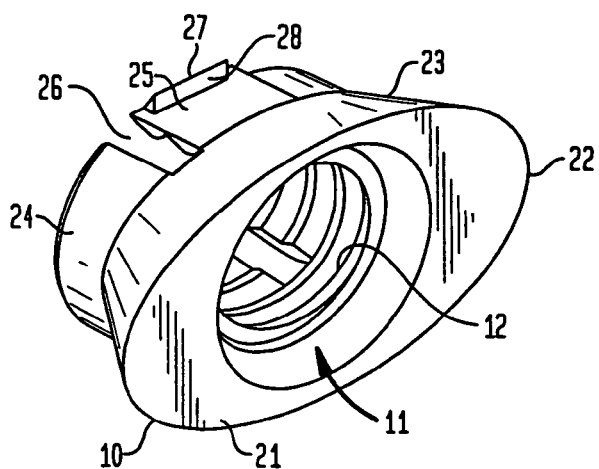
FIG. 5 is a perspective view of a first insert to be used with a load-bearing element according to FIG. 1.

FIG. 1 shows a top view of a load-bearing element in the form of a plate 1 with a row of attachment bores 2 arranged along the longitudinal direction of plate 1 according to a first embodiment of the invention. Bores 2 are through-bores that exhibit an oval central opening 3. At opening 3 there are two side walls 5 on opposite sides of axis 4 which extend parallel to the direction of longitudinal axis 4 of plate 1 and extend at right angles to the surfaces of the plate. These parallel side walls 5 are connected on both ends by semicircular walls 6, each forming a semi-cylindrical boundary so that together the aforementioned oval opening 3 results.

In other forms of the invention, oval bores 2 can also be provided. Bores 2 can also be elliptical or of a common elongated form. What is essential is the multiplicity of functions for the selection of attachment elements or fasteners made possible by insert 10 shown in FIG. 5. Through the mostly elongated form of plate 1, elongated bores 2 are preferred over circular bores in order to maintain flexibility with the insertion of screws with larger diameters. In one embodiment not shown in the drawings, the bore may be essentially cylindrical with the disadvantage that the insert has less material for providing inclined holes in the insert. The elongated form that is asymmetrical with respect to axis 13 (FIG. 4) but rather is symmetrical only with respect to one of the long axes 4 and the flat surfaces enclosing axis 13 actually provides the opportunity, through suitable inserts (see FIGS. 10 and 11), of firmly fixing defined angles in inclined axes 43 and 53.

Arranged around the not necessarily circular or cylindrical walls 5, 6 forming opening 3 is chamfered surface area 7, extending and tapering inwardly from the upper surface 8 of plate 1 that faces away from the bone during implantation. The form of this area 7 can be more easily seen in the cross-section of FIG. 2 and is preferably part-spherical.

FIG. 2 shows a sectional side view of the load bearing element or bone plate 1 according to FIG. 1. Similar characteristics appear in all figures with the same reference numerals. From FIG. 2, one can clearly see in a preferred embodiment, tapered area 7 in the longitudinal direction of axis 4, forms an angle of 37.5 degrees with surface 8. This results in an angle of 142.5 degrees to side walls 5, 6. Naturally, other angles are also possible, particularly it would be possible to have a bore 2 that has no chamfered area 7, which would thus exhibit a purely cylindrical or oval-cylindrical inner boundary surface. The top surface 8 of load-bearing element 1 is formed somewhat deeper in the side area 18 near bores 2. The same is true for upper edge 15 of side wall 5, which are shown to be lower (closer to the plate bottom surface) in a direction opposite the bore ends in longitudinal direction 4. Bottom surface 9, which is closest to the bone in insertion during surgery is here locally flat. Normally, plates 1 can exhibit continuous surfaces 8 and undersurfaces 9 which at each point, for the function of positioning on the bone can always be considered to be flat. But here too, positioning on curved or bent surfaces can be provided.

FIG. 3 shows a top view of the load-bearing element or plate 1 according to FIG. 1 with insert 10 located in bore 2. Each insert 10 is designed to be shaped complementary to bore 2 for locking therein with respect to areas 7 and side walls 5. Insert 10 has a central bore 11 with an internal threading 12.

FIG. 4 shows a sectional side view of the load-bearing element 1 with insert 10 according to FIG. 3 therein. For this, a first embodiment for insert 10 was selected in which main axis 13 of central bore 11 runs perpendicular to surface 8. In the preferred embodiment, insert 10 has an area 19 that extends beyond lower surface 9 that is adjacent the bone. In particular, insert 10 has locking mechanisms that are better shown in FIG. 5 and are not visible in FIG. 4 because they are along its edges. In particular, the locking mechanism can be two projecting rims that engage the underside of plate 1 after the insertion of insert 10. This will be explained in more detail in connection with FIGS. 5 to 11. In any event, insert 10, when it is inserted into plate 1, with its extension area 19, forms a distance spacer with regard to the bone material into which a screw that has been inserted into bore 11 is turned.

FIG. 5 shows a perspective view of an insert 10 to be used with a load-bearing element 1 according to FIG. 1. The reference numeral 21 refers to the surface of insert 10 having a circumference 22 that meets with the edge of area 18 of plate 1. In the preferred embodiment, a spherical surface 23 extends downwardly from surface 21 and is shaped so as to have complementary surface contact with surface 7. In cutting this recess by means of spherical cutting spherical areas are formed in surface 23. Semicircular extension 24 extends downwardly from surface 23 and is in conforming contact, without any significant play, with area 6 of bore 2.

The area lying opposite the longitudinal surface 5 consists of a resilient extension 25 on each side, in which, in the preferred embodiment shown, each extension 25 is provided with slots 26. Each extension 25 has, on its lower edge, a projecting rim 27 facing outward from the point of view of the insert with an upward-facing shoulder 28 with an outer edge 29. Preferably, projecting rim 27 is only slightly rounded in going toward shoulder 28. The surface of rim 27 that is facing toward the bone is then preferably inclined. Extension 25 is also to a certain extent, flexible. In inserting insert 10, extension 25 then slides into bore 2 and is deflected inwardly by the projecting rim 27. Once insert 10 is completely inserted, shoulder 28 slides against underside 9 of plate 1 and locks insert 10 in plate 1. This locking is additionally ensured by the subsequent insertion of a bone screw (not shown). Through the pressure of the screw on the internal thread of extension 25 inward deflection of extension 25 is prevented so that projecting rim 27 is secured under plate 1.

It should be noted that extension 25 and with it projecting rim 27 need not necessarily be arranged as two extensions 25 on the opposing longer sides of insert 10. The design can also include resilient extensions on the narrow sides of an insert, i.e. corresponding to the location of the semicircular cylindrical extensions 24. Extensions 25 can also be arranged in an alternating manner. There can also be only one or two more extensions.

Figure 12:
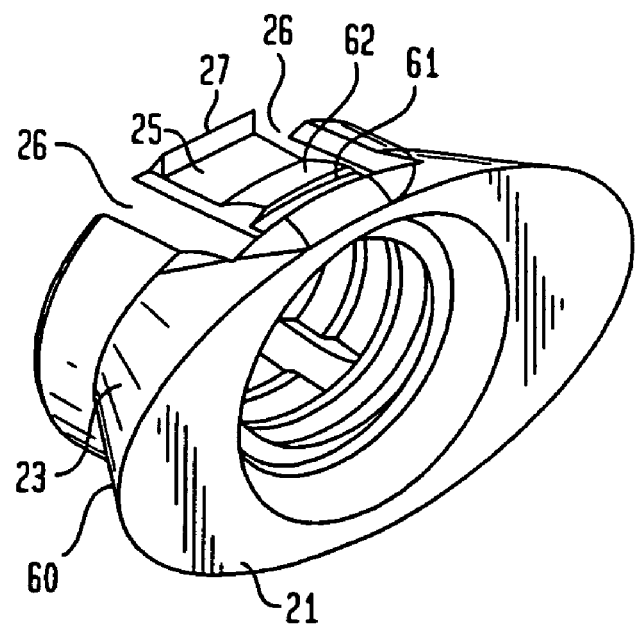
FIG. 12 is a perspective view of an insert modified from that in FIG. 5 for use with a load-bearing element according to FIG. 1 or FIG. 8

Extensions 25 can act as spacers. This can be even further accentuated, as shown in FIG. 12.

Figure 6:
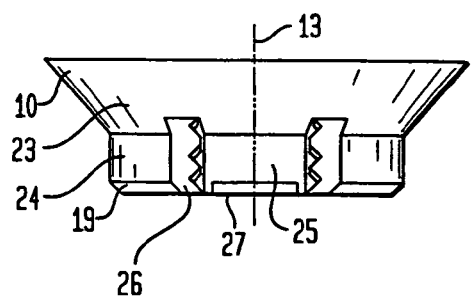
FIG. 6 is a side view of the long side of the insert according to FIG. 5.

FIG. 6 shows a side view of insert 10 according to FIG. 5. Extension section 19 is provided in side areas 7. The projecting rim 27 is formed on an end area of extension 25. Slots 26 extend to the area of spherical surface 23. Of course slots 26 can also be designed to be shorter or longer.

Figure 7:
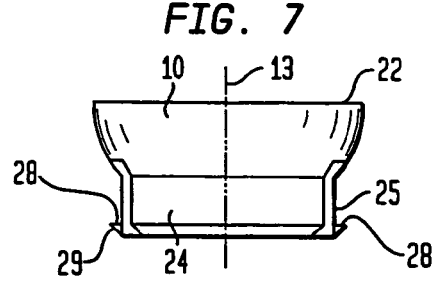
FIG. 7 is a side view of the narrow side of the insert according to FIG. 5.

FIG. 7 shows a side view of the narrow side of insert 10 according to FIG. 5.

Figure 8:
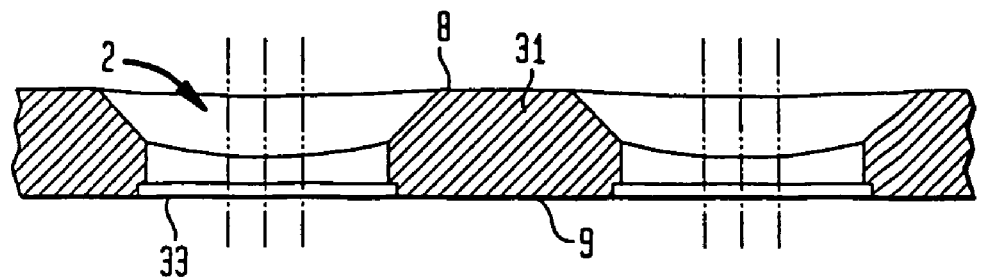
FIG. 8 is a sectional side view of a load-bearing element according to a second embodiment of the invention.
Figure 9:
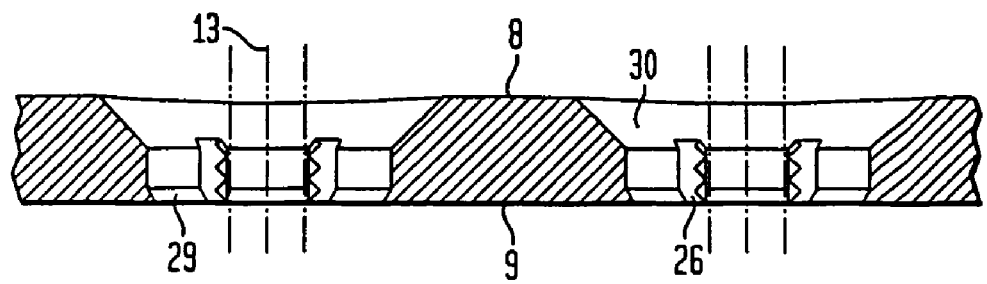
FIG. 9 is a sectional side view of a load-bearing element according to FIG. 8 with an insert inserted according to the second embodiment.

FIG. 8 shows a cross-sectional view of a load-bearing element 31 according to a second embodiment of the invention and FIG. 9 shows a top view of the load-bearing element 31 according to FIG. 8 with insert 30 inserted according to the second embodiment. The difference between the first and second embodiments is that in the second embodiment at least along the length of the longitudinal axis 4 of the load-bearing element 31 is that recess 33 is provided on the bottom surface 9 around opening 2. This recess can also be provided on the narrow side, as shown in FIG. 8. In addition, insert 30 is provided with a projecting rim 27 that is arranged in such a way that the bottom of insert 30 does not project beyond lower surface 9. The underside 29 of insert 30 is thus at least flush with the aforementioned surface 9 of the load-bearing element 1. Otherwise, the resilient engagement of insert 30 in recess 2 is designed in the same way as the engagement of the first embodiment. But here, if desired, the underside 29 of insert 30 can extend beyond the aforementioned surface 9 of the load-bearing element.

FIG. 9 shows a sectional side view of load-bearing element or bone plate 31 according to FIG. 8 with insert 30 according to the second sample embodiment inserted therein.

Figure 10:
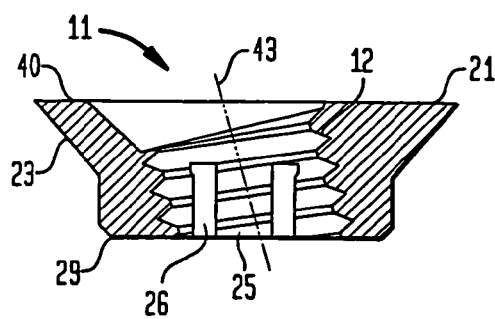
FIG. 10 is a sectional side view of the long side of another insert for use with a load-bearing element according to FIG. 1 or FIG. 8.

FIG. 10 shows a sectional side view of a long side of another insert 40 to be used with a load-bearing element 1 according to FIG. 1 or FIG. 8. Insert 40 preferably has a flush underside 29, but could also be configured similarly to underside 19 and extend beyond plate surface 9. The main difference between insert 40 and the insert shown in FIG. 5 lies in its internal bore 11. Axis 43 of bore 11 is slanted preferably at about 15 degrees in the direction of the longitudinal axis 4. Preferably, in a kit provided for surgery, there would be a series of different inserts with various angles, of, for example 5, 10, 15 and 20 degrees, to name a few possible values. As bores 2 are symmetrical with respect to axis 13, and relatively symmetrical with respect to the perpendicular to the longitudinal axis 4, inserts 40 can be inserted turned 180 degrees. Thus, each insert with a specified angle of, for example, 15 degrees, can be inserted at a plus 15 degree or a minus 15 degree angle.

Figure 11:
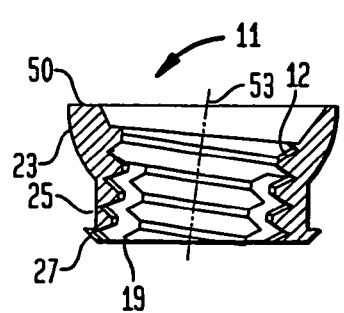
FIG. 11 is a sectional side view of the narrow side of yet another insert for use with a load-bearing element according to FIG. 1 or FIG. 8.

FIG. 11 shows a sectional side view of a narrow side of yet another insert 50 to be used with a load-bearing element 1 according to FIG. 1 or FIG. 8. The preferred insert 50 has an underside 19 extending beyond the bottom plate surface 9 but could also be configured similarly to underside 29 and be flush with the bottom plate surface. The main difference between alternate insert 50 and the insert shown in FIG. 5 lies in its internal bore 11. Axis 53 of bore 11 is shown to be inclined in the direction toward longitudinal axis 4 for example at an incline of 5 degrees, i.e. in a plane perpendicular to the offset shown in FIG. 10. Preferably, in a set provided for surgery, there would be a series of different inserts with various angles, of, for example, 2.5, 5, 7.5 and 10 degrees, to name a few possible values. As bores 2 are symmetrical with respect to axis 13, and relatively so with respect to the longitudinal axis 4, inserts 50 can be inserted turned 180 degrees, so that having each insert with a specified angle, the corresponding "negative" angle is also covered. The angles provided for the embodiments of insert 50 according to FIG. 11 are significantly smaller, since the bore width is less than the length. The angle is about half the size than in the sample embodiments of insert 40 according to FIG. 10. This is because axis 53 is angled perpendicular to the elongated portion of load-bearing element 1 and bore 2, such that there is less room in the insert for the bore to be angled. Generally, steep angles are not necessary, as fixation elements such as screws are generally arranged in essentially the same and/or similar angles to load-bearing element 1. It is also possible to provide inserts inclined in both the aforementioned directions (i.e. with inclines corresponding to axis 43 and axis 53) of FIGS. 10, 11, respectively.

FIG. 12 shows a perspective view of an insert 60 which is modified from insert 10 according to FIG. 5. Insert 60 may to be used with a load-bearing element 1 according to FIG. 1 or FIG. 8. Reference 61 refers to a groove that is set into extension 25 to increase resilience. Groove 61 runs between two slots 26. As discussed above, surface 23, forming a spherical base with respect to upper surface 21, is built in so as to have complementary surface contact to surface 7. In the embodiment according to FIG. 12, groove 61 is set at the upper end area of slit 26, in order to allow the maximum spring action. This produces an area 62 from which extends spherical area 23.

Although the described drawings already show a whole series of possible configurations of the invention, the invention is and should be limited only by the parameters of the attached claims.

The advantage of the invention is that it offers the surgeon, with a plate 1 with conventional standard bores 2, the possibility of forming a plurality of angularly-stable mono-axial bore by means of an inset, and furthermore, that this is made possible intra-operatively.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantable orthopedic device comprising an elongated load-bearing element having a bone contacting surface and having at least one elongate opening for receiving a fixation element, said elongate opening having a circumference with two semi-cylindrical curved end portions separated by straight portions a recessed upwardly facing surface around the opening, said recessed upwardly facing surface tapering towards the bone contacting surface from a first to a second smaller cross-section and a one-piece elongate insert for insertion in the opening wherein the insert exhibits a continuous external portion that is generally complementary to the recessed upwardly facing surface and having a resilient extension complimentary to an internal surface in the straight portion of the elongate opening and having semi-cylindrical extensions adjacent the two semi-cylindrical end portions which, when inserted in the elongate opening are in conforming contact with the two semi-cylindrical end portions of the elongate opening, the straight portion extending from the second smaller cross-section toward the bone contacting surface, the extension having two sidewalls on opposite sides of, and parallel to, an axis which extends parallel to a longitudinal axis of the elongated load bearing element and the sidewalls extend at right angles to the bone contacting surface and wherein the insert exhibits a central through-bore for mounting the body of the fixation element, and in which a surface adjacent the bone contacting surface surrounding the straight portion of the elongate opening is flat and is recessed or forms part of the bone contacting surface wherein the resilient extension of the insert exhibits at least one projection having an upwardly facing surface for extending along the flat surface surrounding the straight portions of the elongate opening for holding the insert in the opening.

2. The device as set forth in claim 1 wherein the insert projection is mounted on the sidewalls so that each projection extend along free ends of the two sidewalls of the insert internal portion.

3. The device as set forth in claim 2 wherein the two sidewalls form a planar side of the insert and the projection is inclined to a principal plane of the load-bearing element along the axis and the extension includes a groove running in a plane parallel to the principal plane of the load-bearing element.

4. The device as set forth in claim 3 wherein the projection interacts with a complementary area in the area of the bottom surface of the load-bearing element.

5. The device as set forth in claim 1 wherein the central through-bore of the insert exhibits an inclined axis that deviates from an axis normal to the principal plane of the load-bearing element, in which the aforementioned inclined axis is inclined towards a narrow side of the load-bearing element and/or in the direction of the longitudinal axis of the load-bearing element.

6. The device as set forth in claim 1 wherein the insert and opening are elongated in a longitudinal direction of the load bearing element.

7. A bone stabilization device comprising:
an elongated bone plate having a plurality of apertures extending through the bone plate, at least one of said apertures having a recessed surface which is arranged around the aperture and which extends and tapers inwardly from a larger cross-section at an upper surface of said load-bearing element to a smaller cross-section, the apertures having curved end walls separated by two planar side walls on opposite sides of and parallel to an axis which extends parallel to a longitudinal axis of the elongated bone plate, the sidewalls extending perpendicularly to a bone contacting surface from the smaller cross-section of the recessed surface and at least one one-piece insert having a body with a threaded bore and a first portion with a continuous outer surface complimentary to the recessed surface of said aperture and a second portion having an outer surface complimentary to said sidewalls of said aperture, at least part of said aperture is surrounded by a flat bottom surface and said insert second portion outer surface having curved end walls for placement upon insertion adjacent the curved end walls of the aperture, the insert curved end walls in conforming contact with the curved end walls of the aperture and two planar resilient sidewalls extending parallel to the two planar sidewalls of the aperture and each sidewall including a projection for engaging said bottom surface.

8. The bone stabilization device as set forth in claim 7 wherein said aperture has a central axis extending from a top plate surface to a bottom plate surface and said bore in said insert has a central axis inclined with respect to said aperture central axis.

9. The bone stabilization device as set forth in claim 7 wherein the aperture is in the form of an elongate slot.

10. The bone stabilization device as set forth in claim 9 wherein said insert second portion has an elongate outer surface for placement adjacent an elongate inner surface of said slot and said projection on the two resilient planar sidewalls extends along said adjacent inner slot surfaces.

11. The bone stabilization device as set forth in claim 10 wherein said bottom surface is a ledge formed around at least the planar walls of said inner surface of said aperture and said resilient projection engaging said ledge.

12. An implantable orthopedic device comprising an elongated load-bearing element, having a bone contacting surface and an opposite upper surface and at least one elongated opening between said two surfaces, at least one fixation element, and at least one one-piece insert exhibiting a central through-bore for mounting the body of the fixation element, wherein said at least one elongated opening of the load-bearing element comprises internal surfaces including two curved end walls separated by two planar side walls perpendicular to the bone contacting surface which extend on opposite sides of and parallel to an axis which extends parallel to a longitudinal axis of the elongated load bearing element and at right angles to the bone contacting surface and a recessed surface surrounding the elongated opening extending from the planar side walls tapering outwardly to the upper surface of the load-bearing element, wherein said insert, when inserted in said opening, exhibits an external form including a continuous first portion complimentary to the outwardly tapered recessed surface surrounding the opening and a second portion including curved end walls in conforming contact with the curved end walls of the elongated opening and two inwardly deflectable planar sidewalls that are generally complementary to the two planar sidewalls of the internal surfaces of the elongate opening and at least one inwardly deflectable sidewall portion including a projection, which projection has an upwardly facing surface which extends along a flat surface of the load-bearing element adjacent the elongate opening which flat surface is recessed from or forms part of the bone contacting surface of the load-bearing element.

13. The device as set forth in claim 12 wherein the insert or the projection extends along each sidewall of the insert.

14. The device as set forth in claim 13 wherein the planar sidewalls are configured in a flexible manner in the inner direction of the opening of the load-bearing element, the sidewalls including a groove running in a principal plane of the load-bearing element.

15. The device as set forth in claim 14 wherein the projection extends away from the central through-bore for interaction with the load-bearing element, the projection extending outwardly of the opening sidewall when the insert sidewall conforms with the opening sidewall.

16. The device as set forth in claim 12, wherein the insert can be fixed in the load-bearing element by means of a fixation element in the opening and remain in the load bearing element and cannot be released until the aforementioned fixation element has been removed from the opening.

17. The device as set forth in claim 12 wherein the load-bearing element exhibits at least one recess on the bottom surface of the load-bearing element adjacent the elongate opening sidewalls, in which the projection can be received, so that the insert, does not extend beyond the bone contacting surface.

18. The device as set forth in claim 12 wherein the central through-bore of the insert exhibits an inclined axis that deviates from an axis normal to the principal plane of the load-bearing element, in which the aforementioned inclined axis is inclined towards a narrow side of the load-bearing element and/or in the direction of the longitudinal axis of the load-bearing element.

19. The device as set forth in claim 12 wherein the insert and opening are elongated in the longitudinal direction of the elongated load bearing element.

* * * * *